Aug. 23, 1938. J. H. NICOLAS Plant Pat. 285
ROSE
Filed June 18, 1937
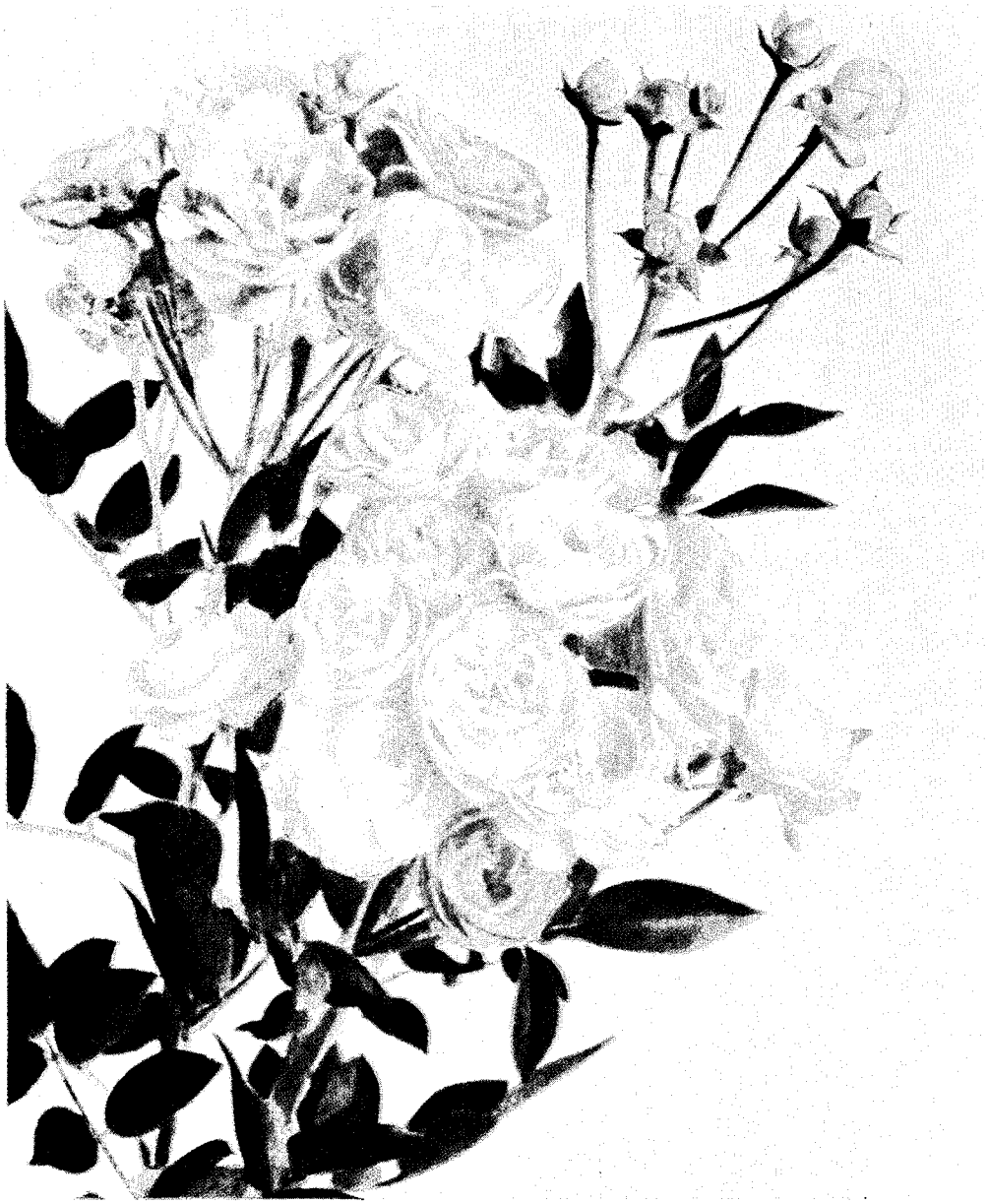
Inventor
Jean H. Nicolas
By Robb & Robb
Attorneys Patented Aug. 23, 1938

UNITED STATES PATENT OFFICE

285

ROSE

Jean H. Nicolas, Newark, N. Y., assignor to Jackson & Perkins Company, Newark, N. Y.

Application June 18, 1937, Serial No. 149,016

1 Claim. (Cl. 47—61)

The present invention relates to a new and distinct variety of rose plant, the result of definite efforts to supply the demand of the florist trade for a new type of polyantha suitable for pot culture. The main requirement of this demand was a moderately growing plant forming a round well balanced head when grown in pots.

Most of the polyanthas heretofore used by florists have been sports, mainly from the Orleans strain that are irregular in growth. These sports are also subject to color variations, reversions and discoloration. I came to the conclusion that these factors could be altered through hybridization and rigid selection of offsprings for recombination.

In carrying out the objective, I selected for the seed parent the variety Baby Tausendschoen because in most respects this variety possessed the characters desired except the flower was most unattractive. The problem mostly before me was, therefore, to effectively transform the flower of this well known variety without much, if any, alteration of the plant characters thereof.

In the origination of the present invention, my first step was to make a large number of crosses of Gloria Mundi on Baby Tausendschoen, but none of this first generation progeny came up to my expectations or the requirements.

I, therefore, selected one plant from the lot which was seeding freely, the $F_2$ seedling of the cross, and replanted the seeds as my second step. From these second generation seedlings, seven were selected as worthy of more extensive tests.

Plants of the selected group were then distributed to various parts of the country and from the reported results, the new variety herein disclosed was selected as the fulfillment of the requirements and constitutes a new type of polyantha adaptable for "forcing" in pots or tubs.

The variety has been budded for several years and always comes true to the original selected seedling.

Its novelty and distinctiveness resides mainly in the color of the bloom which is a brilliant cerise and which holds well, showing little difference between old and new blooms. The individual flowers are full and do not flatten. For garden use, this variety is very useful not only for mass planting where a medium low and uniform growth is desired, but also for bordering or low hedging.

The following is a detail description of the new variety, reference therein to color according with the Gravereaux color standard:—

Parentage:
$F_2$ seedling of the cross of Gloria Mundi on Baby Tausendschoen.

Classification:
*Botanic.*—Polyantha Pompon.
*Commercial.*—Polyantha.

*Flower*

Blooming habit:
Observations made in Jackson & Perkins fields and florists' greenhouses.
Recurrent—Continuous.

Bud:
*Size.*—Small.
*Form.*—Ovoid. Is not affected by wet or hot weather.
*Color.*—When sepals first divide—cerise. When petals begin to unfurl—cerise. When half blown—purpled pink.
*Sepals.*—Smooth edge. Curl back when bud unfurls.
*Calyx.*—Shape—funnel. Size—small. Aspect—smooth. Odor when rubbed—none.
*Peduncle.*— Length — short. Aspect — rough. Color—light green. Strength—stiff.
*Opening.*—Bud opens well. Is not affected by adverse conditions.

Bloom:
*Size.*—Small. Average size when fully expanded—1½ inches.
*Borne.*—In irregular clusters.
*Stems.*—Medium length, strong.
*Form.*—Globular. Retains its form to the end.
*Petalage.*—Double (full but open center).
*Color.*—Center of flower—purpled pink. Outer petals—cerise. Base of petals—cerise. Inside of petals—purpled pink. Reverse of petals—cerise. General tonality from a distance—cerise.
*Variegations.*—None.
*Discoloration.*—No discoloration at end of first, second or third days.

Petals:
*Texture.*—Thick. Is not affected by wet or hot weather.
*Appearance.*—Inside and outside, satiny.
*Form.*—Round.
*Arrangement.*—Imbricated. Petaloids in center—few.
*Persistence.*—Drop off cleanly.
*Fragrance.*—None.
*Lasting quality on the plant and as cut flower.*—Very long.

Genital organs:

*Stamens, anthers.*—Small, many. Color—canary. Arrangement—regular around styles.

*Stamens, filaments (threads).*—Short. Color—yellow.

*Pollen.*—Lemon.

*Styles.*—Columnar.

*Stigmas.*—White.

*Ovaries.*—All enclosed in calyx.

Fruit:

Variety is generally sterile with its own pollen.

*Form.*—Round.

*Aspect.*—Smooth.

*Color at maturity.*—Crimson.

*Sepals.*—Caducous.

*Plant*

Form:

Bush.

Growth:

Medium, compact, dwarf.

Foliage:

Generally seven leaflets.

*Size.*—Small.

*Quantity.*—Abundant.

*Color.*—New foliage—light green. Old foliage—normal green.

*Shape.*—Lanceolate.

*Texture.*—Upper side—glossy. Under side—smooth. Ribs and veins—ordinary.

*Edge.*—Serrated.

*Serration.*—Single, small.

*Rachis.*—Color—green, reddish. Under side—smooth.

*Stipules.*—Medium length, bearded.

*Disease resistance.*—Resistant.

Wood:

*New wood.*—Color—light green. Bark—smooth.

*Old wood.*—Color—green. Bark—smooth.

Thorns (divided into thorns, prickles and short needles):

*Thorns.*—Quantity—on main stalks from base—ordinary. On laterals from stalk—few. Form—broad base, short, hooked downward. Color when young—green and red. Position—irregular.

*Prickles.*—Quantity—on main stalks—few. On laterals—few. Color—green.

*Short needles.*—Quantity—none.

I claim:

A new and distinct type of polyantha rose plant for pot forcing or garden use, characterized by its medium low, uniform growing and brilliant cerise coloring of its flowers, substantially as shown and described.

JEAN H. NICOLAS.